United States Patent
Kularathne et al.

(10) Patent No.: US 11,721,023 B1
(45) Date of Patent: *Aug. 8, 2023

(54) DISTINGUISHING A DISEASE STATE FROM A NON-DISEASE STATE IN AN IMAGE

(71) Applicant: HeHealth PTE Ltd., Singapore (SG)

(72) Inventors: Sembukuttige Yudara Madusanka Kularathne, Singapore (SG); Mathugamavithanage Dilruk Dasantha Perera, Singapore (SG)

(73) Assignee: HeHealth PTE Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/967,696

(22) Filed: Oct. 17, 2022

Related U.S. Application Data

(63) Continuation of application No. 17/959,627, filed on Oct. 4, 2022.

(51) Int. Cl.
*G06T 7/00* (2017.01)
*G06T 7/194* (2017.01)
(Continued)

(52) U.S. Cl.
CPC .......... *G06T 7/0014* (2013.01); *A61B 5/0077* (2013.01); *A61B 5/43* (2013.01); *G06T 5/002* (2013.01); *G06T 5/20* (2013.01); *G06T 7/194* (2017.01); *G06V 10/764* (2022.01); *G06V 10/774* (2022.01); *G06V 20/70* (2022.01);
(Continued)

(58) Field of Classification Search
CPC ......... G06T 5/002; G06T 5/20; G06T 7/0014; G06T 7/194; G06T 2207/20021; G06T 2207/20081; G06T 2207/20132; G06T 2207/20212; G06T 2207/30004; A61B 5/0077; A61B 5/43; G06V 10/764;
(Continued)

(56) References Cited

U.S. PATENT DOCUMENTS

| 8,538,770 | B2 | 9/2013 | Papier et al. |
| 2013/0108179 | A1 * | 5/2013 | Marchesotti ............ G06T 11/60 382/224 |

(Continued)

FOREIGN PATENT DOCUMENTS

WO   WO-2022133590 A1 *  6/2022

*Primary Examiner* — Nay A Maung
*Assistant Examiner* — Jose M Torres
(74) *Attorney, Agent, or Firm* — Sterne, Kessler, Goldstein & Fox, P.L.L.C.

(57) ABSTRACT

Disclosed herein are system, method, and computer program product embodiments for distinguishing a disease state from a non-disease state in an image. An embodiment operates by receiving an image of a target area over a network. The embodiment then corrects for background noise in the image by applying a semantic segmentation filter to obtain a segmented image. The sematic segmentation filter may be trained to remove the background noise from the image. The embodiment then determines, using a trained artificial intelligence (AI) model and the segmented image, at least one classification for the target area. The embodiment finally causes the display of the at least one classification and disease information on a user device associated with a user. The trained AI model may be trained using at least augmented images obtained from a set of images to correct for at least an imbalance in the set of images.

20 Claims, 12 Drawing Sheets

(51) Int. Cl.
*G06T 5/20* (2006.01)
*G06V 10/764* (2022.01)
*G06V 10/774* (2022.01)
*G06V 20/70* (2022.01)
*G16H 30/40* (2018.01)
*G16H 50/20* (2018.01)
*G06T 5/00* (2006.01)
*A61B 5/00* (2006.01)

(52) U.S. Cl.
CPC ............ *G16H 30/40* (2018.01); *G16H 50/20* (2018.01); *G06T 2207/20021* (2013.01); *G06T 2207/20081* (2013.01); *G06T 2207/20132* (2013.01); *G06T 2207/20212* (2013.01); *G06T 2207/30004* (2013.01); *G06V 2201/03* (2022.01)

(58) Field of Classification Search
CPC .. G06V 10/774; G06V 20/70; G06V 2201/03; G16H 30/40; G16H 50/20
See application file for complete search history.

(56) References Cited

U.S. PATENT DOCUMENTS

| | | | |
|---|---|---|---|
| 2016/0232425 A1* | 8/2016 | Huang | G06T 7/40 |
| 2017/0018075 A1* | 1/2017 | Middlebrooks | G06N 5/045 |
| 2018/0189949 A1 | 7/2018 | Lapiere et al. | |
| 2019/0073770 A1* | 3/2019 | Moradi | G06N 3/045 |
| 2020/0194108 A1* | 6/2020 | Podilchuk | G16H 30/40 |
| 2020/0211188 A1* | 7/2020 | Gao | G06N 3/08 |
| 2021/0118133 A1 | 4/2021 | Benkert | |
| 2021/0133970 A1 | 5/2021 | Abid et al. | |
| 2022/0093270 A1* | 3/2022 | Gheorghita | G06N 3/08 |

\* cited by examiner

Normalized confusion matrix 1000

| True label 1004 | Gentital_warts | HSV | Normal | Penile_cancer | Penile_candidiasis | Syphillis |
|---|---|---|---|---|---|---|
| Gentital_warts | 0.96 | 0.02 | 0.00 | 0.00 | 0.00 | 0.02 |
| HSV | 0.05 | 0.93 | 0.00 | 0.00 | 0.00 | 0.02 |
| Normal | 0.00 | 0.02 | 0.98 | 0.00 | 0.00 | 0.00 |
| Penile_cancer | 0.07 | 0.03 | 0.03 | 0.79 | 0.03 | 0.03 |
| Penile_candidiasis | 0.07 | 0.00 | 0.00 | 0.05 | 0.88 | 0.00 |
| Syphillis | 0.00 | 0.08 | 0.03 | 0.03 | 0.00 | 0.86 |

Predicted label 1002

FIG. 10

DISTINGUISHING A DISEASE STATE FROM A NON-DISEASE STATE IN AN IMAGE

RELATED APPLICATION

This application is a continuation of U.S. patent application Ser. No. 17/959,627, filed Oct. 4, 2022, now pending, and is incorporated by reference in its entirety.

FIELD

The present disclosure is generally directed to distinguishing disease state from a non-disease state in an image, and more particularly to detecting a disease state in the image using an artificial intelligence model.

BACKGROUND

Infectious diseases such as sexually transmitted diseases (STDs) are a health concern worldwide. Delays in diagnosing and providing treatments result in an increased risk of transmission between individuals and a poor prognosis for an affected individual. Conventionally, diagnostic and testing are performed after consultation with a doctor. However, such consultation can discourage some individuals from getting tested due to patient sensitivity (e.g., fear of results, privacy concerns, feeling of shame). In addition, individuals in rural or remote communities often do not have access to care because of distances they must travel. And even if individuals are able to consult with a doctor, many doctors rely on laboratories that are unable to handle the different types of tests required for disease screening. Diagnosing diseases via a screening tool at home provides several benefits to users by providing early diagnostic and access to treatment that may save lives. However, conventional image analysis approaches to disease screening suffer from various technological problems.

First, such approaches can be highly inaccurate because the images often include background noise. Second, such approaches are often highly inaccurate because determining the correct parameters to guide the image analysis in distinguishing between disease state and non-disease state is often challenging. For example, determining the correct parameters for an artificial intelligence (AI) model that accurately detects one or more diseases in an image of an area of interest may require training the AI model using a large dataset. However, in the technological field of medical imaging, a large dataset may not be available and may not be balanced (e.g., due to the rarity of some diseases). Third, such approaches often involve having to expend significant computational resources to determine the correct parameters to guide the image analysis in distinguishing between disease state and non-disease state. Fourth, such approaches may be inaccurate over time because the parameters guiding the image analysis in distinguishing between disease state and non-disease state often need to be refined based on changes in the individual population and/or changes is disease presentation. Finally, such approaches may suffer from a lack of privacy due to an association between the image and an identity of the individual.

SUMMARY

Provided herein are system, apparatus, article of manufacture, method and/or computer program product embodiments, and/or combinations and sub-combinations thereof, for efficiently and accurately distinguishing a disease state from a non-disease state in an image.

In some embodiments, a method for efficiently distinguishing a disease state from a non-disease state in an image includes receiving over a network from a user device associated with a user, an image of a target area of the user and correcting for background noise in the image by applying a semantic segmentation filter to obtain a segmented image. The sematic segmentation filter is trained to remove the background noise from the image. The method also includes determining, using a trained artificial intelligence (AI) model and the segmented image, at least one classification for the target area and causing the display of the at least one classification and disease information on the user device associated with the user. The trained AI model is trained using at least augmented images obtained from a set of images to correct for at least an imbalance in the set of images. The at least one augmented image is indicative of a disease state and is obtained from another image indicative of a non-disease state. The trained AI model is further trained using a feedback comprising the at least one classification.

In some embodiments, a system for efficiently distinguishing a disease state from a non-disease state in an image includes a memory and at least one processor coupled to the memory. The at least one processor is configured to receive, over a network from a user device associated with a user, an image of a target area of the user and correct for background noise in the image by applying a semantic segmentation filter to obtain a segmented image. The sematic segmentation filter is trained to remove the background noise from the image. The at least one processor is configured to determine, using a trained artificial intelligence (AI) model and the segmented image, at least one classification for the target area and cause the display of the at least one classification and disease information on the user device associated with the user. The trained AI model is trained using at least augmented images obtained from a set of images to correct for at least an imbalance in the set of images and at least one augmented image is indicative of a disease state and is obtained from another image indicative of a non-disease state. The trained AI model is further trained using a feedback comprising the at least one classification.

Further features of the present disclosure, as well as the structure and operation of various embodiments, are described in detail below with reference to the accompanying drawings. It is noted that the present disclosure is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated herein and form part of the specification, illustrate the present disclosure and, together with the description, further serve to explain the principles of the present disclosure and to enable a person skilled in the relevant art(s) to make and use embodiments described herein.

FIG. 10 is a schematic that shows a normalized confusion matrix of an artificial intelligence (AI) model, according to some embodiments.

Figure 1A:
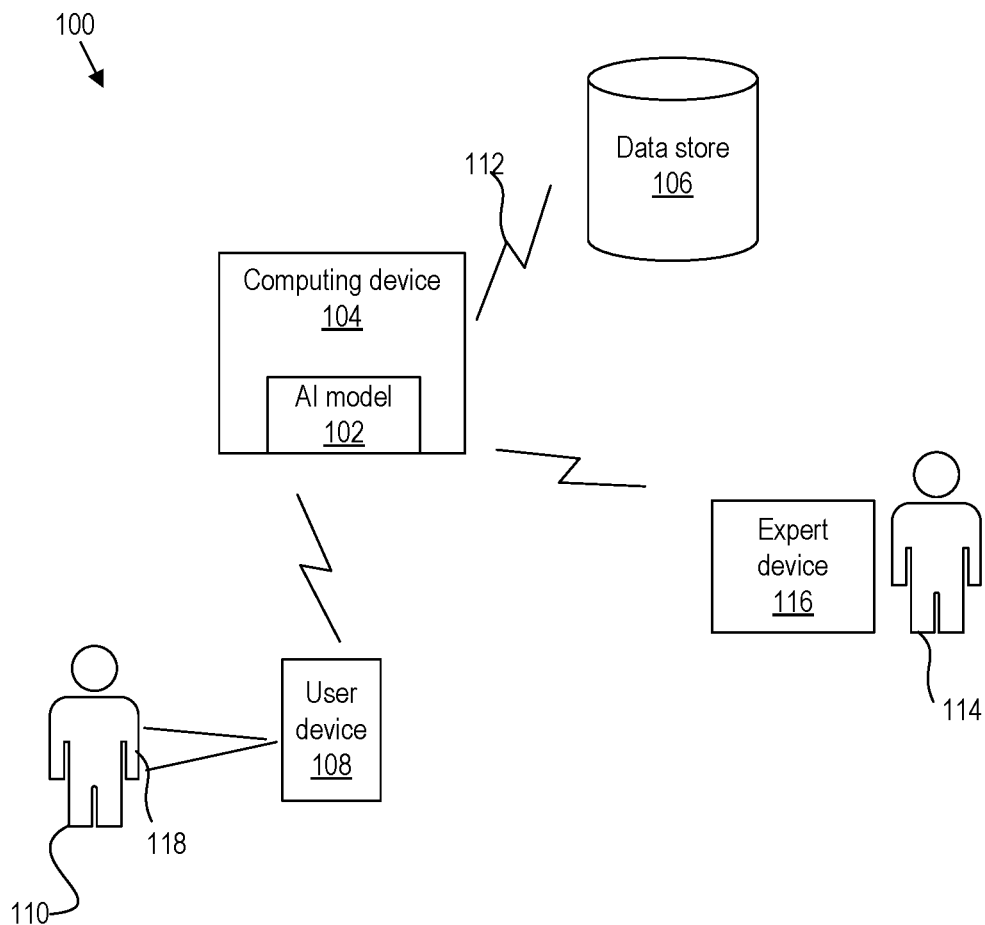
FIG. 1A is a schematic that illustrates a system for distinguishing disease state from a non-disease state in an image, according to some embodiments.

The features of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements. Additionally, generally, the left-most digit(s) of a reference number identifies the drawing in which the reference number first appears. Unless otherwise indicated, the drawings provided throughout the disclosure should not be interpreted as to-scale drawings.

DETAILED DESCRIPTION

This specification discloses one or more embodiments that incorporate the features of the present disclosure. The disclosed embodiment(s) are provided as examples. The scope of the present disclosure is not limited to the disclosed embodiment(s). Claimed features are defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Spatially relative terms, such as "beneath," "below," "lower," "above," "on," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The term "about," "approximately," or the like may be used herein to indicate a value of a quantity that may vary or be found to be within a range of values, based on a particular technology. Based on the particular technology, the terms may indicate a value of a given quantity that is within, for example, 1-20% of the value (e.g., ±1%, ±5%±10%, ±15%, or ±20% of the value).

Embodiments of the disclosure may be implemented in hardware, firmware, software, or any combination thereof. Embodiments of the disclosure may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, and/or instructions may be described herein as performing certain actions. However, it should be appreciated that such descriptions are merely for convenience and that such actions in fact result from computing devices, processors, controllers, or other devices executing the firmware, software, routines, instructions, etc. In the context of computer storage media, the term "non-transitory" may be used herein to describe all forms of computer readable media, with the sole exception being a transitory, propagating signal.

Aspects of the present disclosure relate to distinguishing a disease state from a non-disease state in an image. In particular, the present disclosure relates to an artificial intelligence (AI) model that classifies the image as corresponding to a disease state or a non-disease state. It improves the technological field of medical imaging and the functioning of computing systems that are designed to detect and to classify diseases from images as described further below.

Despite an extensive image search, statistics of an initial dataset of healthy and non-healthy image indicate that there is a lack of availability of valid images corresponding to various sexually transmitted diseases (STDs) over the internet. This may be due to the sensitive and restrictive nature of these images and the difficulty in validating the images. Furthermore, there is a class imbalance among different disease categories. That is, there is a considerable variance among the number of images per class. For example, some diseases such as penile cancer are rare and therefore the availability of images that are indicative of penile cancer is low. In addition, the dataset is not representative. For example, validated images for a particular skin complexion may be rare or non-existent. Thus, the AI model suffers from a lack of accuracy when the AI model is trained using (a) a small dataset, (b) a non-representative dataset, and (c) an imbalanced dataset (e.g., imbalance between images corresponding to different diseases due to the rarity of some diseases).

In addition, images submitted for analysis are often self-captured. Therefore, the image may suffer from background noise that reduces the accuracy of the classification (diagnosis) and the training of the AI model. For example, a considerable number of available images are of low quality due to noisy backgrounds (e.g., trouser zipper, watermarks on backgrounds). In addition, the image may include other body parts (e.g., fingers holding the area of interest). However, as discussed above, input images for training the AI model are limited. Therefore, unlike other image prediction tasks, low-quality images may not be discarded.

The present disclosure provides an improvement in the technology of medical imaging by providing an improved trained AI model that solves the above-noted technological problems. In particular, the usefulness of the existing technology (e.g., medical imaging) is extended into groups or classes having a weak or non-existing training dataset. The present disclosure solves the above-noted challenges by creating synthetic data for training the AI model. The synthetic data may be obtained using a layered image augmentation. This can mitigate the lack of images (e.g., a small dataset) and the imbalance between diseases and group/class. As described below, the layered image augmentation can be automatically adjusted to improve the efficiency of underperforming classes.

Further, the present disclosure solves the technological problem of limited availability of data (e.g., a small dataset) by modifying layers of conventional AI models by reducing the overall complexity of the model. Thus, the functionality of the computer is also improved by minimizing the computational resources called for during the training phase and the distinguishing or classification phase. Whereas previously, training the model or providing a classification to the user would take longer, aspects of the present disclosure allow the classification and training to occur more quickly, improving speed and timeliness of the classification. The approaches described herein employs a novel architecture that allows the model to provide accurate results with minimal computing resources.

The accuracy of the AI model is continuously improved by providing a feedback to the AI model that improves the accuracy by increasing the size of the dataset using validated image-classification sets. For example, a first training set comprising a collected set of images and augmented set of images is created and used to train the AI model. Then, a second training set comprising the validated image-classification sets and the collected set of images and augmented set of images is used to continuously retrain the AI model, as described further below. A validated image-classification may refer to an image and corresponding classification that have been confirmed or verified by a medical expert.

In addition, the present disclosure solves the technological problem of background noise in self-captured photos rooted in the technical field of medical imaging. The present disclosure provides a semantic segmentation based filter that removes the background noise and zooms on the area of interest, whereas previously, the AI model may try to classify an image that includes other body parts that lower the accuracy rate and increase the processing time. The semantic segmentation based filter overcomes the problem specifically arising in self-captured images for medical imaging by filtering pixels that are not associated with the area of interest for the medical imaging. In addition, by overcoming this technological problem, the dataset used in training the AI model is enlarged as images of low quality (e.g., those having background noise) are filtered and used in the training instead of being discarded.

In addition to the technological improvements and advantages described above, the present disclosure provides the technological advantage of protecting the privacy of the user. The users do not have privacy concerns, as the uploaded images are not associated with any identification that may be traced to an identity of the user. Thus, users are non-hesitant to upload the image that provides the advantage of early diagnostic.

The approaches described herein may be used to classify and detect many diseases. For example, the diseases may include STDs, dermatologic conditions, cancer, and/or any disease that may be detected visually (e.g., without laboratory testing).

FIG. 1 is a block diagram of a system 100 for efficiently distinguishing a disease state from a non-disease state in an image, according to some embodiments.

System 100 may include a computing device 104 and a data source 106. The computing device may include an AI model 102. In some embodiments, the computing device 104 may be configured to receive an input from a user 110. The user 110 may capture an image of an area of interest 118 (e.g., target area, body part of interest) using a user device 108. The user 110 may upload the image to the computing device 104 for analysis via a network 112. For example, the user may submit one or more images of a genital area to screen for STDs in the genital area. In some aspects, the user device 108 may include an electronic device. The electronic device can be any of a variety of devices, such as a smart phone, a cellular phone, a personal digital assistant, a tablet computer, a notebook computer, a laptop computer, a desktop computer, or a combination thereof. The user device 108 may include an image capture module or a sensor (e.g., a camera). The user device 108 may include a communication module (not shown) for electronic communication with the network 112. In some embodiments, the user 110 may submit two or more images to the computing device 104. In this case, the computing device 104 may disregard images with low quality (e.g., out focus, low resolution). In some aspects, the computing device 104 may select the higher quality image between the two or more images to further process. The image is uploaded to the computing device 104 without any patient identifier. Thus, the privacy of the user 110 is preserved. For example, the image may be associated with a randomly generated number that may identify the user device 108 or a smartphone (mobile) application running on the user device 108. The randomly generated number is not associated with the identity of the user.

The user 110 may interact with the computing device 104 via a mobile application installed on the user device 108, a website that may be accessed from the user device 108, or other communication interface. The computing device 104 may be a cloud-based computing device (e.g., Amazon Web Services®) accessed via an application programming interface (API).

Based in part on the image, the computing device 104 may be configured to determine a classification corresponding to the image. For example, the computing device 104 may determine whether the image correspond to a healthy state or to a non-healthy state. In addition, the computing device 104 may determine one or more diseases that may correspond to the image. In some aspects, the computing device 104 may prompt the user 110 to enter or respond to questions that may be relevant or to help in the classification (e.g., when the symptoms appeared, presence of any pain with the symptoms, or any other symptoms that are associated with the one or more diseases).

The image and the information are analyzed by the AI model 102 to determine at least a classification of the image. The AI model 102 may be a trained convolutional neural network (CNN). The computing device 104 may output the classification to the user device 108. For example, the computing device 104 may output a signal to the user device 108 that causes the user device 108 to display a notification. The notification may include the classification or an indication that the classification is available and can be retrieved by the user.

The AI model 102 may be trained using a dataset. The dataset may comprise a plurality of images associated with male STDs. The images may be collected using partnership with clinicians to obtain consented, labelled images from various sources like hospitals, clinics, and universities. Additionally, an automated web scraping tool may download freely available labelled images over the internet. The dataset includes images associated with visually recognizable diseases (e.g., syphilis, penile candidiasis, penile cancer, herpes simplex viruses (HSV), genital warts and balanitis) and a set of healthy images. The images and corresponding labels are verified by experts in the field. In some aspects, any invalid images may be filtered out and mislabeled images are corrected. As described previously herein, a layered image augmentation approach is used to mitigate both lack of images and class imbalance problems by increasing the size of the dataset. In addition, the trained AI model is further trained using a feedback based on a validated classification (validated image-diagnosis) as described further below.

Not only the computing device 104 may determine the classification, the computing device 104 may send the image to an expert device 116 via the network 112. The expert device 116 may be associated with a medical expert 114. A signal by the computing device 104 may be output to the expert device 116 that causes a notification on the expert device 116 to be displayed. The notification may cause the expert device 116 to display the image submitted by the user 110 along with a plurality of classifications and prompt the medical expert 114 to select one or more classifications. The medical expert 114 may review the image and identify a classification. The input of the medical expert 114 may be uploaded to the computing device 104. Upon receiving the selection of the medical expert 114, the expert device 116 upload the classification to the computing device 104.

In some embodiments, the computing device 104 may output the image and the classification to the expert device 116. The medical expert 114 may review the image and the classification and confirm or revise the classification. The expert device 116 may prompt the expert to enter a validation, for example, an "ok" and "not ok" may be displayed on an interface of the expert device 116 for the medical expert 114 to select. The input of the medical expert 114 may be uploaded to the computing device 104. In some aspects, the expert device 116 may poll the computing device 104 to determine whether images for validation are available. In response to determining that there are images for validation, the expert device 116 may download the images. The expert device 116 may poll the computing device 104 continuously or at predetermined periods (e.g., 30 seconds).

The expert device 116 may include one or more memories, one or more processors, and one or more communication interfaces to receive inputs from the medical expert 114 and to communicate with the computer device 104 via the network 112.

After receiving the classification from the expert device 116, the computing device 104 may revise the classification (determined by the AI model if there is a mismatch) before outputting the classification to the user device 108. In some aspects, the computing device 104 may also add the received classification from the expert and the image to the data source 106 as a validated image. The image and the classification may be used to retrain the AI model 102 as described in details further below.

The user 110 may receive the classification in real time or near real-time. In some aspects, the classification may be a provisional classification. A second classification may be output after validation by the medical expert 114. For example, once the verification is received by the computer device 104, the computer device 104 may output a signal to the user device 108 that causes the user device 108 to display a notification. The notification may include a message to inform the user 110 that the result is verified by the expert. In some aspects, the notification may prompt the user to login to an account to access the result associated with the image.

In some aspects, the results may be presented to the user 110 in two layers. For example, the user device 108 may display information indicating whether the image corresponding to the area of interest 118 corresponds to a disease state or to a non-disease state. Then, if the image corresponds to a disease state, the user 110 may be presented with a possible disease and a corresponding likelihood scores. Additional diseases may also be output. Possible diseases may be ranked based on their corresponding likelihood scores. In some aspects, the likelihood may correspond to a probability that the image indicates a disease and the accuracy of the probability. In some aspects, only the disease that have a likelihood greater than a threshold are presented to the user 110.

In some embodiments, the system 100 may be implemented on a single user product with both client and server components residing on the same computer. That is, the operations of computing device 104 may be performed by the user device 108. A user may download an application to the user device 108 and receive the classification.

In addition to outputting a classification to the user, the user may be presented with a number of tests that may be ordered from home to further validate the classification. In some aspects, upon receiving approval from the user, the computing device 104 may cause a corresponding home test to be dispatched to the user. In some aspects, the user may be referred to a telemedicine service. The computing device 104 may identify the telemedicine service based on a location of the user. The location of the user 110 may be determined using positioning systems such a global positioning system of the user device 108.

Computing device 104 may be communicatively coupled to the data source 106. Data source 106 may be, for example, a data lake. Although, only a single data source 106 is shown, system 100 may include any number of data sources. In some embodiments, the computing device 104 may pull data from data source 106 such as an updated dataset for retraining the AI model 102.

As used herein, an application programming interface ("API") may comprise any software capable of performing an interaction between one or more software components as well as interacting with and/or accessing one or more data storage elements (e.g., server systems, databases, hard drives, and the like). An API may comprise a library that specifies routines, data structures, object classes, variables, and the like. Thus, an API may be formulated in a variety of ways and based upon a variety of specifications or standards, including, for example, POSIX, the MICROSOFT WINDOWS API, a standard library such as C++, a JAVA API, and the like.

In some embodiments, system 100 may be implemented on one or more servers. For example, a server may be a mobile device, a laptop computer, a desktop computer, grid-computing resources, a virtualized computing resource, cloud computing resources, peer-to-peer distributed computing devices, a server farm, or a combination thereof. The servers may be centralized in a single room, distributed across different rooms, distributed across different geographic locations, or embedded within the network 112. The servers can couple with the network 112 to communicate with other devices, such as a client device or a device associated with the user. The client device may be any of a variety of devices, such as a smart phone, a cellular phone, a personal digital assistant, a tablet computer, a notebook computer, a laptop computer, a desktop computer, or a combination thereof. The servers and the client device may be stand-alone devices and work independently from one another.

The network 112 refers to a telecommunications network, such as a wired or wireless network. The network 112 can span and represent a variety of networks and network topologies. For example, the network 112 can include wireless communication, wired communication, optical communication, ultrasonic communication, or a combination thereof. For example, satellite communication, cellular communication, Bluetooth, Infrared Data Association standard (IrDA), wireless fidelity (WiFi), and worldwide interoperability for microwave access (WiMAX) are examples of wireless communication that may be included in the network 112. Cable, Ethernet, digital subscriber line (DSL), fiber optic lines, fiber to the home (FTTH), and plain old telephone service (POTS) are examples of wired communication that may be included in the network 112. Further, the network 112 can traverse a number of topologies and distances. For example, the network 112 can include a direct connection, personal area network (PAN), local area network (LAN), metropolitan area network (MAN), wide area network (WAN), or a combination thereof.

Figure 1B:
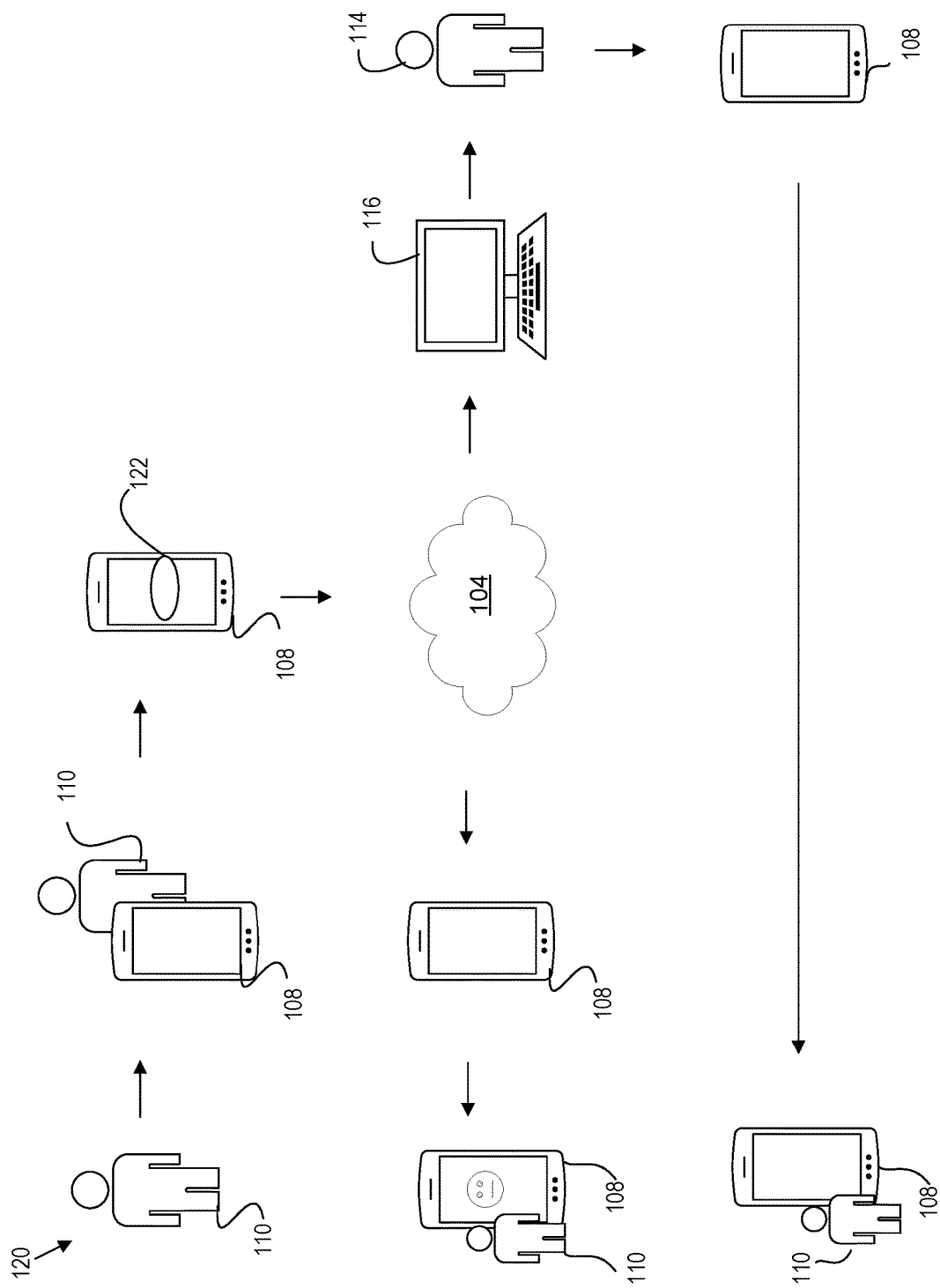
FIG. 1B is a flow diagram that shows the operations of the system for distinguishing a disease state from a non-disease state in an image, according to some embodiments.

FIG. 1B is a flow diagram 120 that shows the operations of the system 100 for distinguishing a disease state from a non-disease state in an image, according to some embodiments. The flow 120 may begin by the user 110 capturing an image of the area of interest 118 using the user device 108. The user 110 may access the imaging capabilities of the user device via the smartphone application associated with the system 100. An image 122 of the area of interest 118 is uploaded to the computing device 104. In some aspects, the computing device 104 may be a cloud-based computing device (e.g., AWS). The computing device may output the classification to the user device 108 and the user 110 can review the classification. The computing device 104 may output the image 122 to the expert device 116 to be reviewed by the medical expert 114. The classification of the medical expert 114 is sent to the user 110 via the smartphone application.

Figure 2:
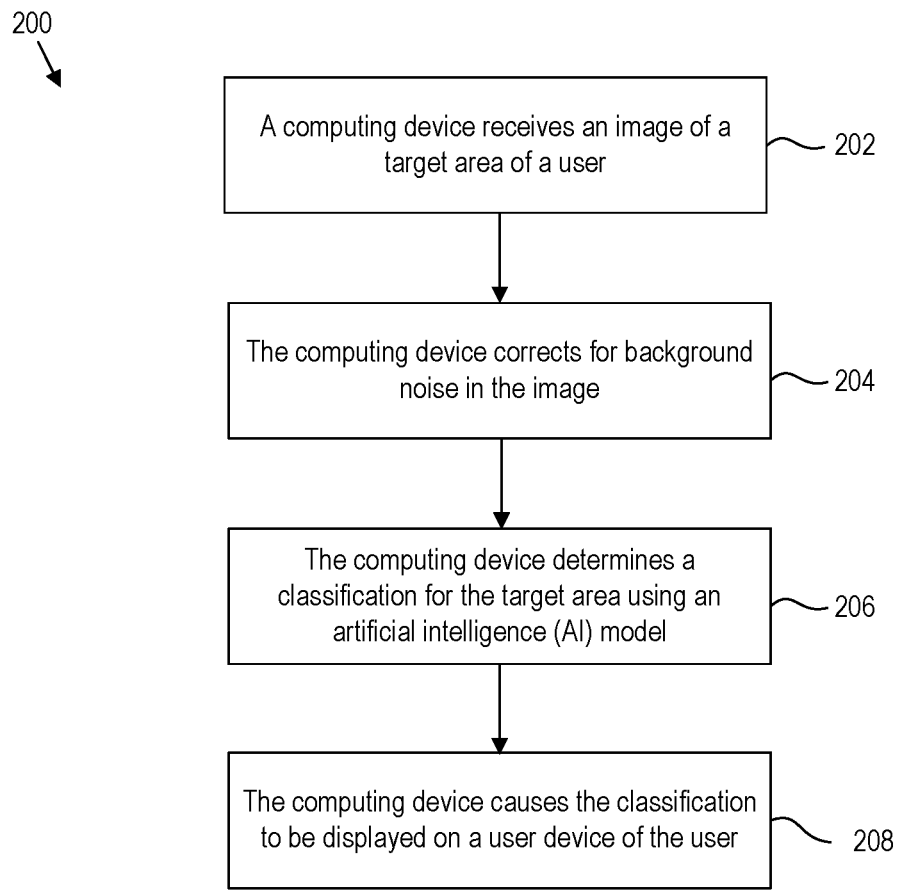
FIG. 2 is a flowchart for a method for distinguishing a disease state from a non-disease state in an image, according to some embodiments.

FIG. 2 is a flowchart for a method 200 for efficiently distinguishing a disease state from a non-disease state in an image, according to an embodiment. Method 200 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 2, as will be understood by a person of ordinary skill in the art.

Method 200 shall be described with reference to FIG. 1. However, method 200 is not limited to that example embodiment.

In 202, computing device 104 receives an image of the target area 118 of the user 110 over the network 112 from the user device 108. For example, the target area may be a male genital area.

In 204, computing device 104 corrects for background noise in the image by applying a semantic segmentation filter to obtain a segmented image. The sematic segmentation filter is trained to remove the background noise from the image. In some embodiments, the sematic segmentation filter removes pixels from the image that are not associated with the target area. The sematic segmentation filter is further described in relation to FIG. 6.

In 206, computing device 104 determines at least one classification for the target area using a trained artificial intelligence (AI) model and the segmented image. The at least one classification may indicate a disease state or a non-disease state. The trained AI model is trained using at least augmented images obtained from a set of images to correct for at least an imbalance in the set of images. At least one augmented image is indicative of a disease state and is obtained from another image indicative of a non-disease state. In addition, the at least augmented images may include one or more transformations for the images of the dataset. Data augmentation is further described in relation to FIG. 3.

In 208, computing device 104 causes the display of the at least one classification and disease information on the user device 108 associated with the user 118. In some aspects, the disease information may include a corresponding probability. In some aspects, computing device 104 may output two or more classifications. For example, when the difference between the probability of two classifications is below a threshold, the computing device 104 may output two classifications to the user. The disease information may also include a description of the disease and possible treatments. In addition, the disease information may include a list or referral for further testing to confirm the classification.

The classification may be used to re-train the AI model. For example, a validated classification (e.g., by a medical expert) may be added to the training dataset (e.g., stored in the data store 106). The AI model may be retrained using the training dataset in response to determining that a number of newly added images exceeds a threshold. In some aspects, the training dataset may be retrained at preset periods (e.g., monthly). In addition, the image may be augmented as described above. For example, the image may be augmented in response to determining that the image corresponds to an underrepresented disease in the dataset.

Figure 3:
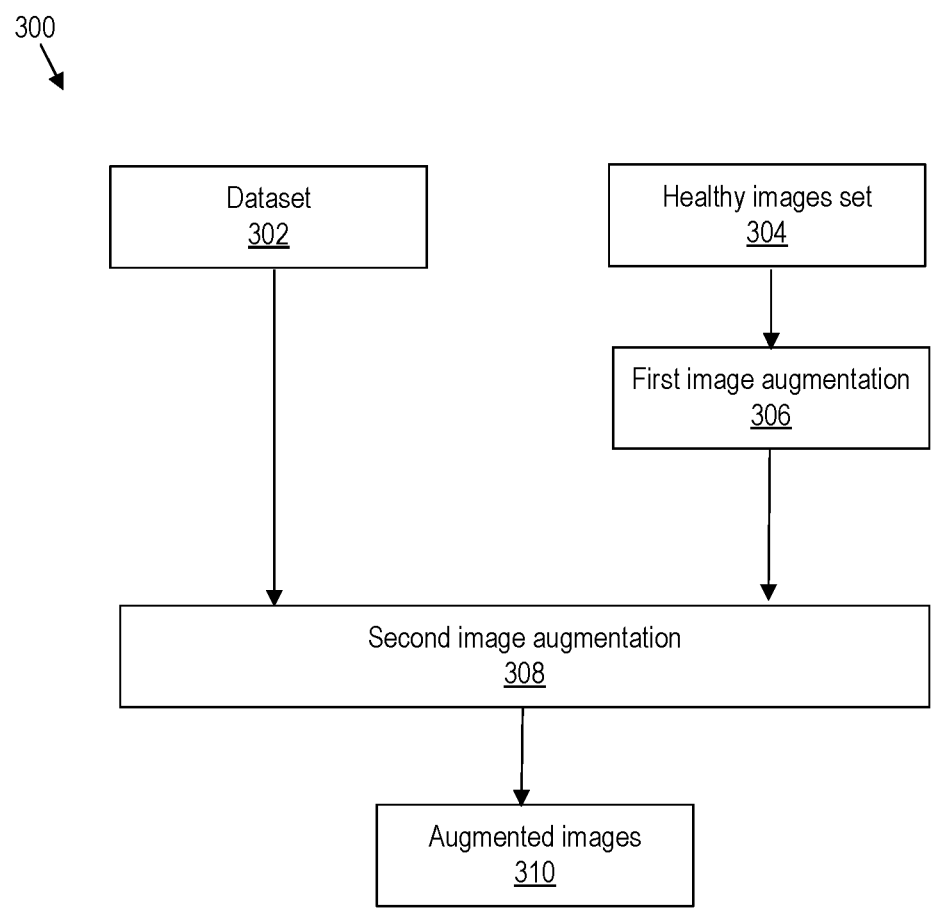
FIG. 3 is a flow diagram that illustrates an image augmentation process, according to some embodiments.

FIG. 3 is a schematic that illustrates an image augmentation flow 300, according to some embodiments. Dataset 302 may include a plurality of images. The plurality of images may correspond to different possible classifications of the target area. For example, the plurality of images may include healthy images of the target area (non-disease state) and images associated with a disease state. The images corresponding to the disease state may correspond to a plurality of diseases. An additional set of healthy images 304 may be acquired (e.g., images corresponding to a non-disease state). The additional set of healthy images 304 may be used to obtain additional images (synthetic image) associated with disease states that may be used for training the AI model (e.g., AI model 102).

The additional images associated with disease states may be obtained by performing a first image augmentation 306 on the images of the healthy images set 304. Augmented diseased images may be obtained by first extracting specific visually recognizable disease patterns for each disease category and blending them on a healthy image by considering various visual and clinical factors such as disease location, skin complexion, and orientation of the body part or target area.

In addition or alternatively to the first image augmentation 306, a second image augmentation 308 may be performed. The second image augmentation 308 may be performed on the images from the dataset 302 and the augmented images obtained after the first image augmentation 306. The random image augmentation 308 may include one or more transformations to each of the images of the dataset 302 and the augmented images. The one or more transformations include rescaling, rotating, vertical flipping, horizontal flipping, vertical shifting, horizontal shifting, slanting a shape of an image, changing a brightness level of the image, and changing a zoom level of the image. The augmented images 310 (obtained after the second image augmentation 306) may be used to train the AI model (e.g., AI model 102).

Figure 4:
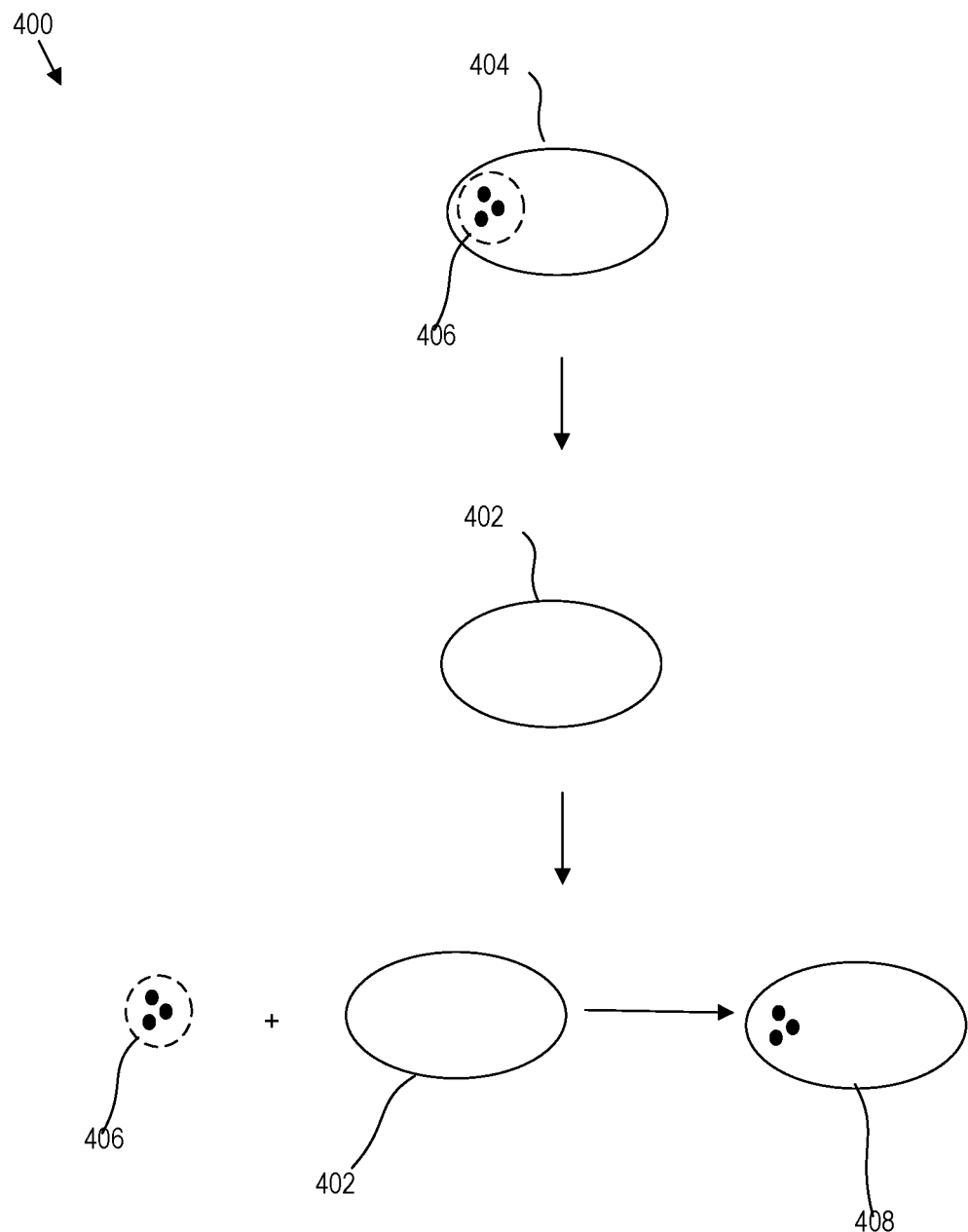
FIG. 4 is a flow diagram that illustrates a first method of image augmentation, according to some embodiments.

FIG. 4 is a schematic that illustrates a flow 400 for a first method of image augmentation, according to some embodiments. The first method of image augmentation may correspond to first image augmentation 306. A disease pattern 406 may be extracted from a first image 404. The first image 404 may correspond to a disease state. The first image 404 may be selected from the dataset 302. Then, a second image 402 corresponding to a non-disease state is identified. The second image 402 may be identified from the healthy images set 304 based on one or more factors including a skin complexion (e.g., color, texture). A suitable location and orientation in the second image 402 may be identified. The suitable location may be identified by detecting the area of interest in the second image 402 and matching the position of the disease pattern 406 relative to the area of interest in the first image 404. The disease pattern 406 may be blended with the second image 402 at the suitable location and orientation to obtain an augmented image 408. In some aspects, once the first image augmentation 306 is completed, the augmented images may be verified by an expert (e.g., a medical expert may confirm that the augmented image corresponds to the disease state from which the disease pattern is indicative). Once the validity of the images is verified, the images may be added to the dataset 302.

As described above, healthy images are augmented to obtain images corresponding to different disease states. In addition to using augmented images to solve the technical problem of a small dataset, augmentation may be used to correct for the imbalance in the dataset. The number of augmented images that correspond to a classification or class may be selected based on the imbalance in the dataset. The imbalance may be between the images corresponding to a particular disease (e.g., penile cancer versus syphilis) and/or between the skin complexion (e.g., fair skin versus dark skin). A higher number of augmented images corresponding to a dark skin complexion with a first disease may be used in the training of the AI model compared to augmented images for a fair skin complexion with the disease. This can be used to correct for the imbalance between skin complexions and improve the accuracy rate even for underrepresented skin complexion.

The number of augmentations per class may be chosen systematically as follows. First, quality disease patterns/patches that are eligible for blending for each disease may be identified. The available images corresponding to the healthy state may be identified and paired with the disease patterns/patches. Then, each pair may be blended to create one augmentation per pair and the AI model (e.g., AI model 102) may be trained using the new dataset (e.g., dataset 302 and the augmented images). The obtained results may be used to compare the performances of each class, and the augmentations for underperforming classes are iteratively increased by a predetermined percentage (e.g., 10%) until the performance of the underperforming classes starts to degrade.

In one example, the augmentations are performed using 150 healthy images that are different from the images in the healthy class in the dataset. Table 1 summarizes the number of augmented images for each classification.

TABLE 1

Number of augmented images for each classification

| Classification | Original image count | Augmented image count |
|---|---|---|
| Syphilis | 190 | 178 |
| Penile candidiasis | 140 | 255 |
| Penile cancer | 211 | 70 |
| Normal | 450 | 0 |
| HSV | 212 | 217 |
| Genital warts | 217 | 227 |
| Balanitis | 150 | 110 |

In addition to creating synthetic data, one or more transformations may be applied to the images. The second image augmentation 308 may randomly apply a selected set of transformations to each image during the training process of the AI model. Each augmented image is obtained from an original image by applying the one or more transformations. Thus, each augmented image is different from the original image (image from dataset 302 or images after the first image augmentation) in one or more aspects depending on the applied transformation (e.g., shifting, rotating, flipping). This provides the advantage of obtaining a more robust model that can effectively predict for unseen images with different image variations. Table 2 below summarizes a list of transformations that may be applied to augment the images. Note that each image (both from dataset 302 and obtained after the first image augmentation 306) is transformed using a randomly selected set of these transformations to obtain the augmented images 310 that are used for training the AI model 102. These transformations are selected by extensive training and testing of the underlying AI model 102 that result in the best model performances across multiple model variations and train/test settings. In some implementations, the image augmentation may be implemented in a deep learning platform such as "KERAS" using the "ImageDataGenerator."

The one or more transformations may include rescaling, rotating, vertical flipping, horizontal flipping, vertical shifting, horizontal shifting, slanting a shape of the image, changing a brightness of the image, and changing a zoom level of the image. In some aspects, the image is rotated through any degree between 0 and 360. The degree of rotation may be randomly chosen. In some aspects, shifting (vertical or horizontal) may be done by adding a constant value to all pixels of the images. The width or height are shifted by the constant value of pixels. The image may also be flipped along the vertical or horizontal axis. In addition, the brightness of the image may be randomly changed. The image may be darkened or brightened. This improves the accuracy as not all images of the area of interest are captured with similar lighting conditions. The zoom level may also be adjusted to zoom in on the image or zoom out on the image. A summary of the list of transformations is shown in table 2.

TABLE 2

List of transformations and corresponding value range

| Transformations | Value range |
| --- | --- |
| Rescale | 1/255 |
| Rotation range | 360 |
| Height shift range | 0.1 |
| Shear range | 0.1 |
| Zoom range | 0.1 |
| Fill mode | 'nearest' |
| Brightness range | [0.9, 1.2] |
| Vertical flip | True |
| Horizontal flip | True |
| Image size | 299 |
| Batch size | 16 |
| Color mode | 'rgb' |
| Class mode | 'categorical' |
| Shuffle | True |

Figure 5:
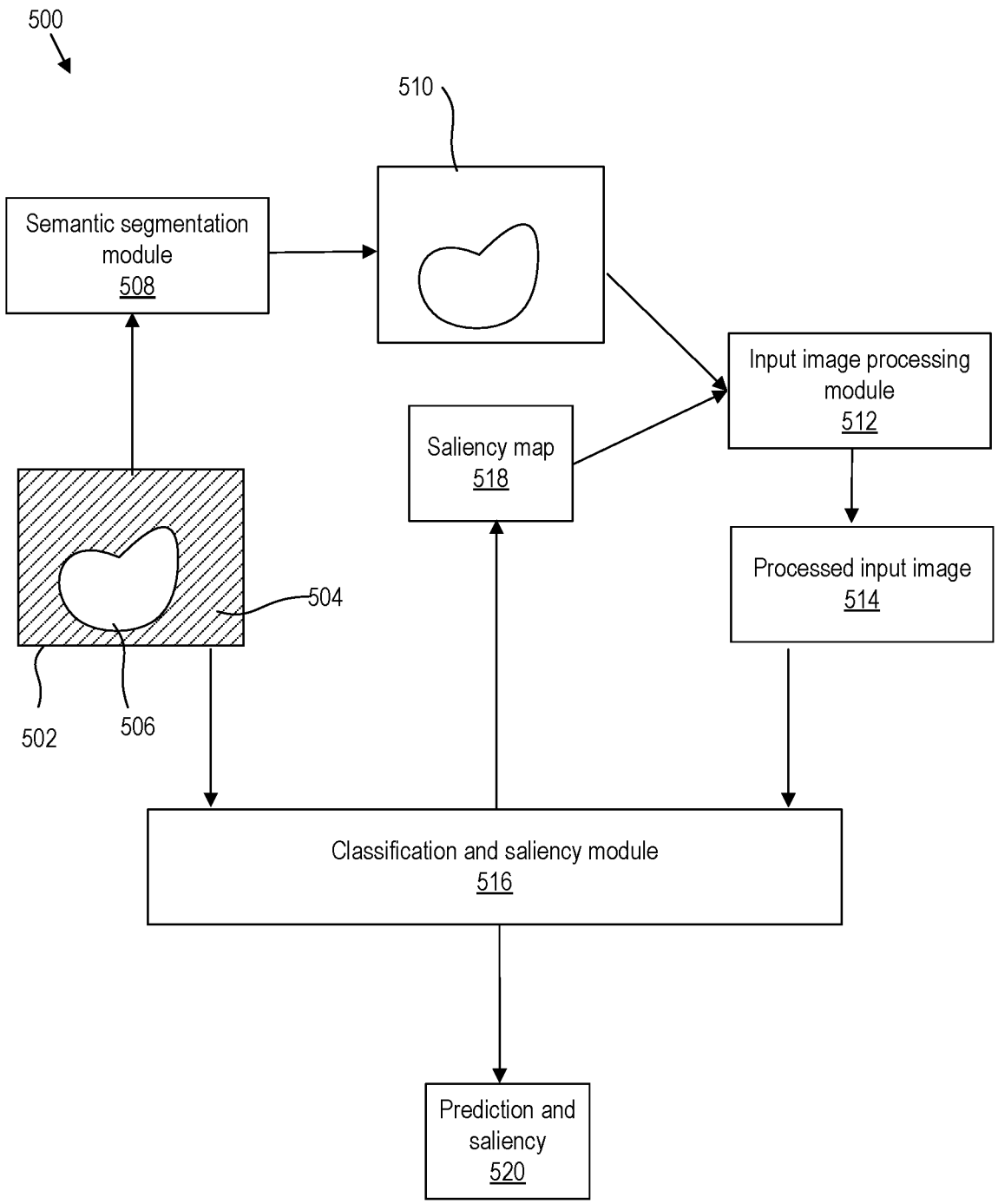
FIG. 5 is a flow diagram that illustrates generating a prediction and a saliency map from an image, according to some embodiments.

FIG. 5 is a schematic that shows a prediction flow 500, according to some embodiments. A user may capture an image 502 that includes an area of interest 506. The area of interest 506 may include a body part. In addition to the area of interest 506, the image 502 may include background noise 504. The image 502 may be passed to a semantic segmentation module to remove the background noise 504 from the image 502. The semantic segmentation module 508 may output a filtered image 510 that includes the area of interest 506 without the background noise 504. This provides the advantage of improving the efficiency and the accuracy of the AI model.

Semantic segmentation (e.g., pixel-based classification) classifies each pixel of the input image as belonging to a particular class. Semantic segmentation module 508 may extract the area of interest (e.g., penis region) and discard any background noise (e.g., underwear, other body parts). The semantic segmentation module 508 may be trained by labelling the pixels in each image of a training dataset (e.g., dataset 302) into a binary value based on the pixel belonging to the area of interest or not. The resulting binary mask may be used as a training label. The semantic segmentation module 508 may be trained as a supervised learning task using an encoder/decoder architecture. The semantic segmentation module 508 may output a filtered image 510.

Using the image 502, a classification and saliency module 516 may determine a saliency map 518 that highlights the area of interest in the image 502.

The saliency map 518 and the filtered image 510 may be passed to an input image-processing module 512 to obtain a processed input image 514. The input image-processing module 512 may identify a bounding box covering all the saliency regions in the saliency map 518. The processed input image 514 may include the pixels of the image 502 that either belong to the filtered image 510 or are included in the bounding box. The remaining pixels may be discarded and are not included in the processed input image 514. This helps remove unnecessary background noise while retaining the significant pixels from the original image (e.g., image 502).

The processed input image 514 outputted by the input image processing module 512 may be input to the classification and saliency module 516. The classification and saliency module 516 may determine a prediction and saliency output 520 that includes a first output and a second output. The first output may correspond to a predicted disease class (1 of 7 classes) and the second output may correspond to a saliency map that highlights the area of interest.

Figure 6:
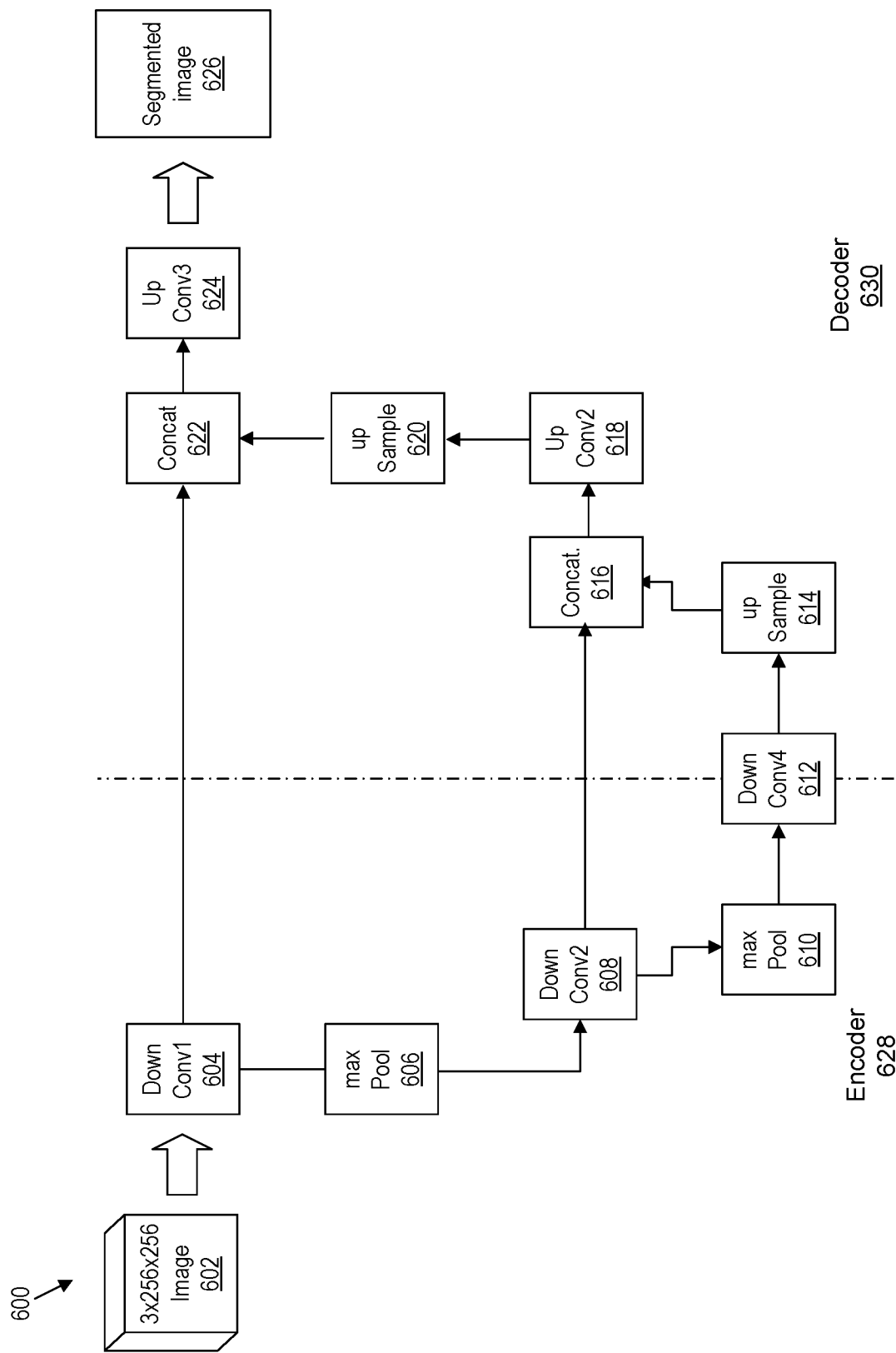
FIG. 6 is a diagram that illustrates an architecture of a semantic segmentation module, according to some embodiments.

FIG. 6 is a schematic that illustrates an architecture diagram of the semantic segmentation module 508, according to some embodiments. The architecture diagram of the supervised learning task is a U-net architecture 600 that is scaled down (removed several layers from conventional U-net architecture) and trained using the dataset to support the simpler binary classification task. The U-net architecture 600 may include an encoder 628 and a decoder 630. The encoder 628 may include a first down convolution 604 followed by a first max pooling operation 606. Then, a second down convolution 608 followed by a second max pool operation 610. The second max pool operation 610 is followed by a third down convolution 612. The first down convolution 604, the second down convolution 608, and the third down convolution 612 can be a two 3×3 convolution. The max pooling operation may be a 2×2 max pooling operation with stride equals to 2 for down-sampling. The decoder 630 may include an up-sampling 614 followed by a concatenation 616 and a first up-convolution 618. The first up-convolution 618 is followed by a second up-sampling 620 and a second concatenation 622. The second concatenation 622 is followed by a second up-convolution 624. The second up-convolution 624 outputs a segmented image 626.

Figure 7:
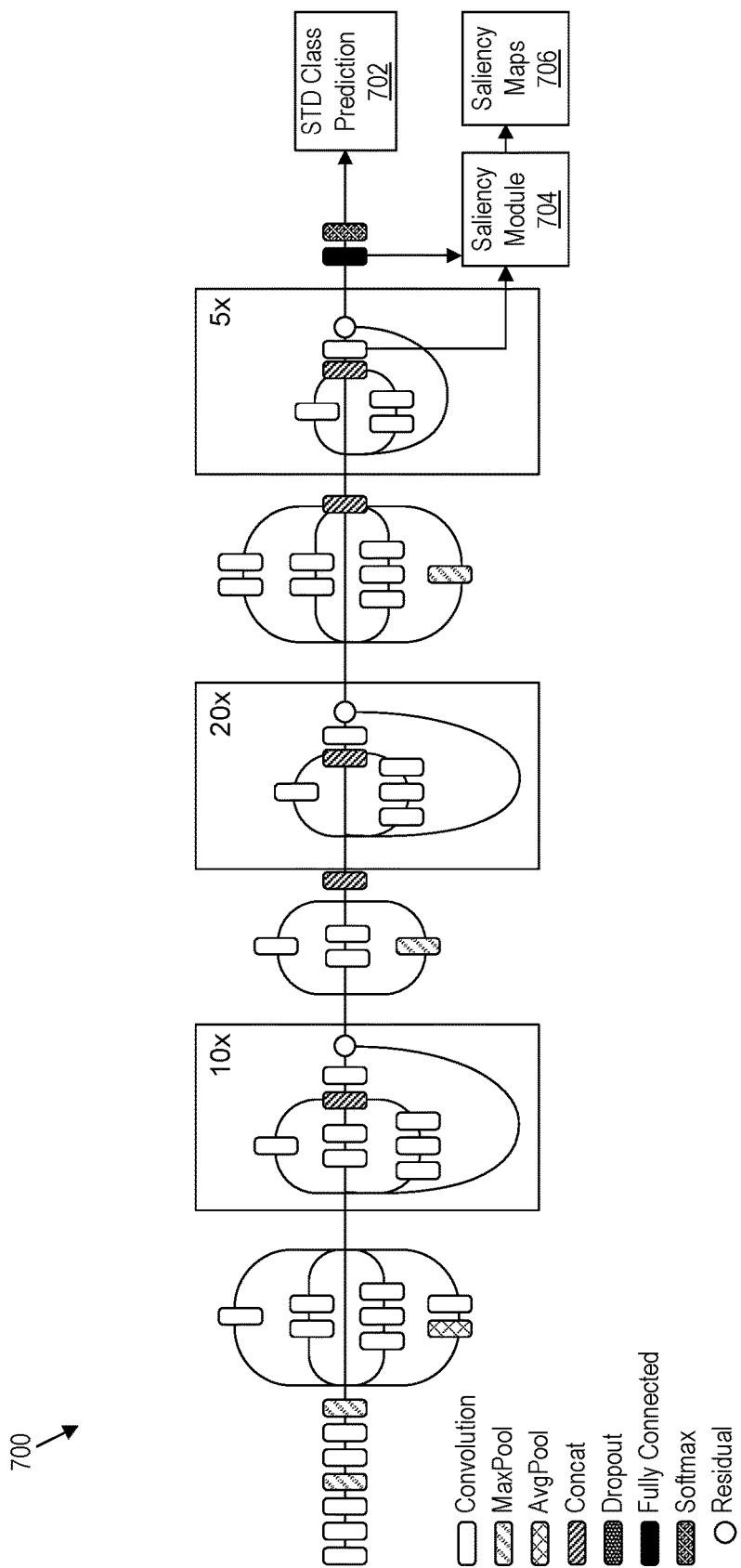
FIG. 7 is a diagram that illustrates an architecture of a classification and saliency module, according to some embodiments.

FIG. 7 is a schematic that shows an architecture 700 for the classification and saliency module 516, according to some embodiments. The classification and saliency module 516 may use a CNN model. The CNN model may be an inception residual network (ResNet) model (e.g., Inception-ResNet-v2). The inception residual network (ResNet) model is updated through testing on the training dataset. Modifications from a base model of an inception-ResNet-v2 are especially designed to both reduce the overall complexity of the model that help learn under limited available data and effectively capture both class prediction and saliency maps. For example, the final layers of the inception-ResNet-v2 model are modified to include one or more layers that determine the saliency map.

In addition, one or more layers of a conventional inception-ResNet-v2 may be removed to reduce the computational cost and provide results in a timely fashion to the user. The one or more layers to be removed may be the underperforming layers. The underperforming layers may be identified by monitoring an accuracy of the model. In addition, the layers associated with detecting features that are not called for in the classification are removed.

Figure 8:
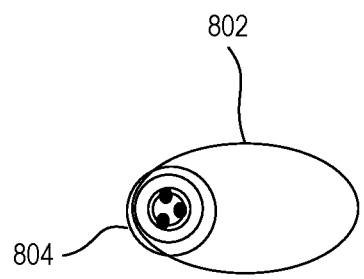
FIG. 8 is a schematic that illustrates a saliency map, according to some embodiments.

As described previously herein, the model outputs two predictions. A first prediction 702 that corresponds to the STD class prediction and a second prediction 706 that corresponds to a saliency prediction (e.g., the saliency map). The saliency map shows the area of interest (e.g., body part) with highlighted regions that corresponds to the primary focus areas of the diseases in input images. An exemplary saliency map is shown in FIG. 8. A saliency module 704 helps users (patients and clinicians) visually recognize the problematic areas with ease. Furthermore, the saliency module 704 acts as an explainable AI module as the saliency module 704 provides a simple visual explanation to the primary output of the classification and saliency module 516 (e.g., the predicted STD class). Including explainable layers in the model provides the advantage of faster training and improved accuracy for the model. This is because the cause of the false classification may be determined. For example, by analyzing the saliency map, it can be determined whether the model is focus on an incorrect area of the image. Thus, the layers that are associated with identifying the area of interest are modified and trained.

The saliency module 704 may use different saliency mapping approaches (e.g., a deconvolutional network approach, a gradient-based approach, a guided backpropagation algorithm, a class activation mapping approach). In some aspects, the saliency module 704 uses a gradient weighted class activation mapping (GradCAM++) approach. As verified by several qualitative evaluations conducted with the help of clinicians and medical experts, the saliency module 704 provides better visual explanations with accurate object localizations and effectively highlighting the occurrences of multiple disease areas in a single image.

Different types of models for weight initializations may be used for inception-ResNet-v2 model. For example, weights may be randomly initialized. Weights may also be initialized using weights that are trained over different visual object recognition tasks (e.g., ImageNet database).

FIG. 8 is a schematic that illustrates a saliency map 802, according to some embodiments. The saliency map 802 highlights a disease area 804. For example, the saliency map 804 may overlay highlighting the disease area 804. One or more attributes of the disease area 804 may be changed based on a spatial support for the predicted class.

Referring back to the training of classification and saliency module 516, the categorical cross entropy may be used as the loss function since the STD class prediction 702 is a multi-class prediction task.

In some aspects, the training set may include 90% of both original and augmented images in each class. The test set may include the remaining 10% of both original and augmented images in each class. Due to the limited availability of training data, the model is partially initialized using weights of other inception-ResNet-v2 models. Specifically, the weights of the early layers of the model that have a similar structure to the inception-ResNet-v2 model are initialized to help speed up the training process.

Figure 9A:
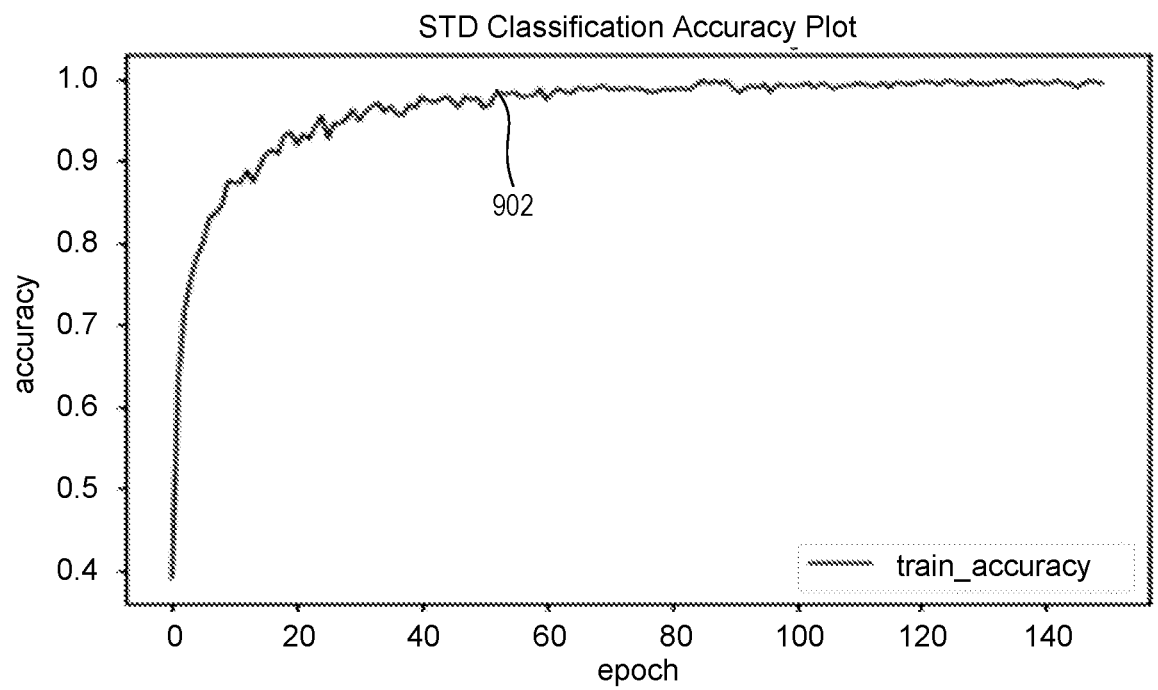
FIG. 9A is a graph that shows the variation of accuracy over the number of training epochs, according to some embodiments.
Figure 9B:
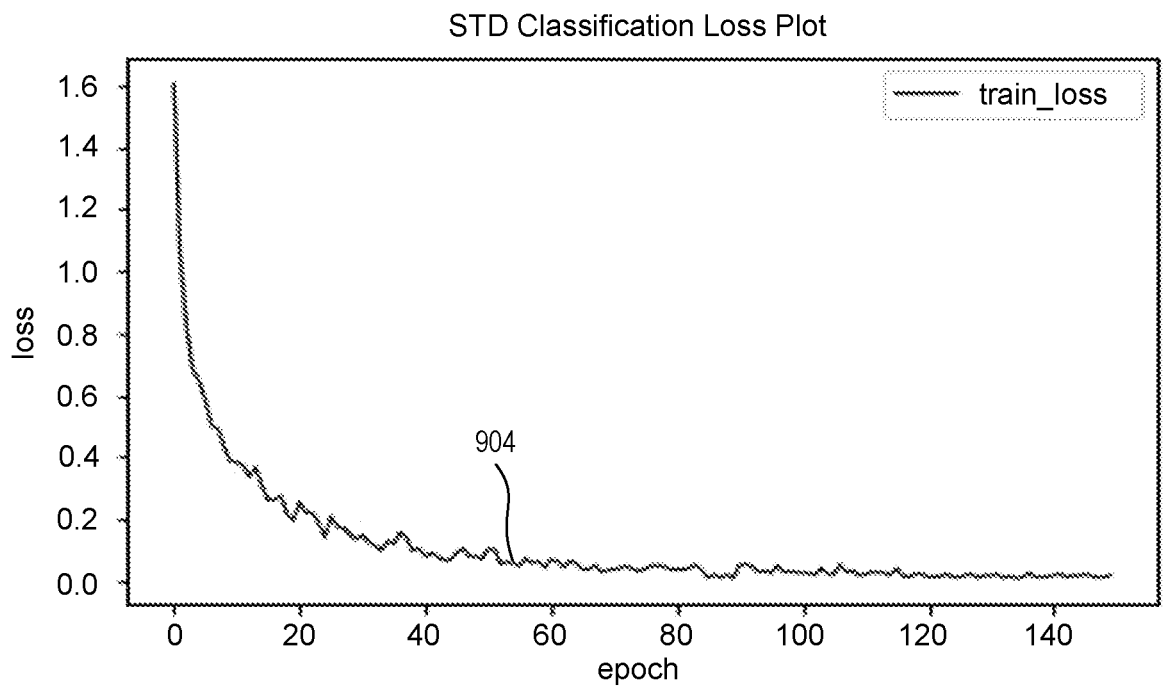
FIG. 9B is a graph that shows the variation of loss over the number of training epochs, according to some embodiments.

In some embodiments, the model is trained for 150 epochs using the Adam optimizer that helps accelerates the gradient descent process. The learning rate and epsilon of the optimizer is set to 0.01 and 0.1, respectively. In one implementation, the model is trained with using a tesla P100 16 Gb GPU provided by a cloud platform (e.g., Kaggle). FIG. 9A is a graph that shows the variation of accuracy over the number of training epochs, according to some embodiments. Trace 902 shows the accuracy with respect to the number of training epochs. FIG. 9B is a graph that shows the variation of loss over the number of training epochs, according to some embodiments. Trace 904 shows the loss with respect to the number of training epochs.

The model is evaluated using a multi-class evaluation metrics such as precision, recall, F1-score, and support. The test set (e.g., 10% of the dataset) is used in the evaluation. The classification results of the model are summarized in table 3 below.

TABLE 3

| Classification report | | | | |
|---|---|---|---|---|
|  | Precision | Recall | F1-score | Support |
| Genital warts | 0.86 | 0.96 | 0.91 | 45 |
| HSV | 0.87 | 0.93 | 0.90 | 43 |
| Normal | 0.96 | 0.98 | 0.97 | 45 |

TABLE 3-continued

| Classification report | | | | |
|---|---|---|---|---|
|  | Precision | Recall | F1-score | Support |
| Penile cancer | 0.88 | 0.79 | 0.84 | 29 |
| Penile candidiasis | 0.97 | 0.88 | 0.92 | 40 |
| Syphilis | 0.91 | 0.86 | 0.89 | 37 |
| Accuracy |  |  | 0.91 | 239 |
| Macro average | 0.91 | 0.90 | 0.90 | 239 |
| Weighted average | 0.91 | 0.91 | 0.91 | 239 |

FIG. 10 is a schematic that shows the normalized confusion matrix 1000 of the model, according to some embodiments. Diagonal elements of the normalized confusion matrix 1000 represent the number of elements for which a predicted label 1002 is equal to a true label 1004. The off-diagonal elements are those that are mislabeled by the system 100. The normalized confusion matrix 1000 may be used to determine whether one or more class is underperforming.

In one example, the approaches described herein achieved a 91% accuracy in accurately and efficiently detecting STD. Note that, both quantitative and qualitative evaluations showcased that despite the influence from Inception-ResNet-v2 and GradCAM++ approaches, the model described herein and the corresponding training process consistently outperformed the Inception-ResNet-v2 and GradCAM++ models and other state-of-the-art models, in terms of both prediction accuracy and effectiveness of the saliency.

Figure 11:
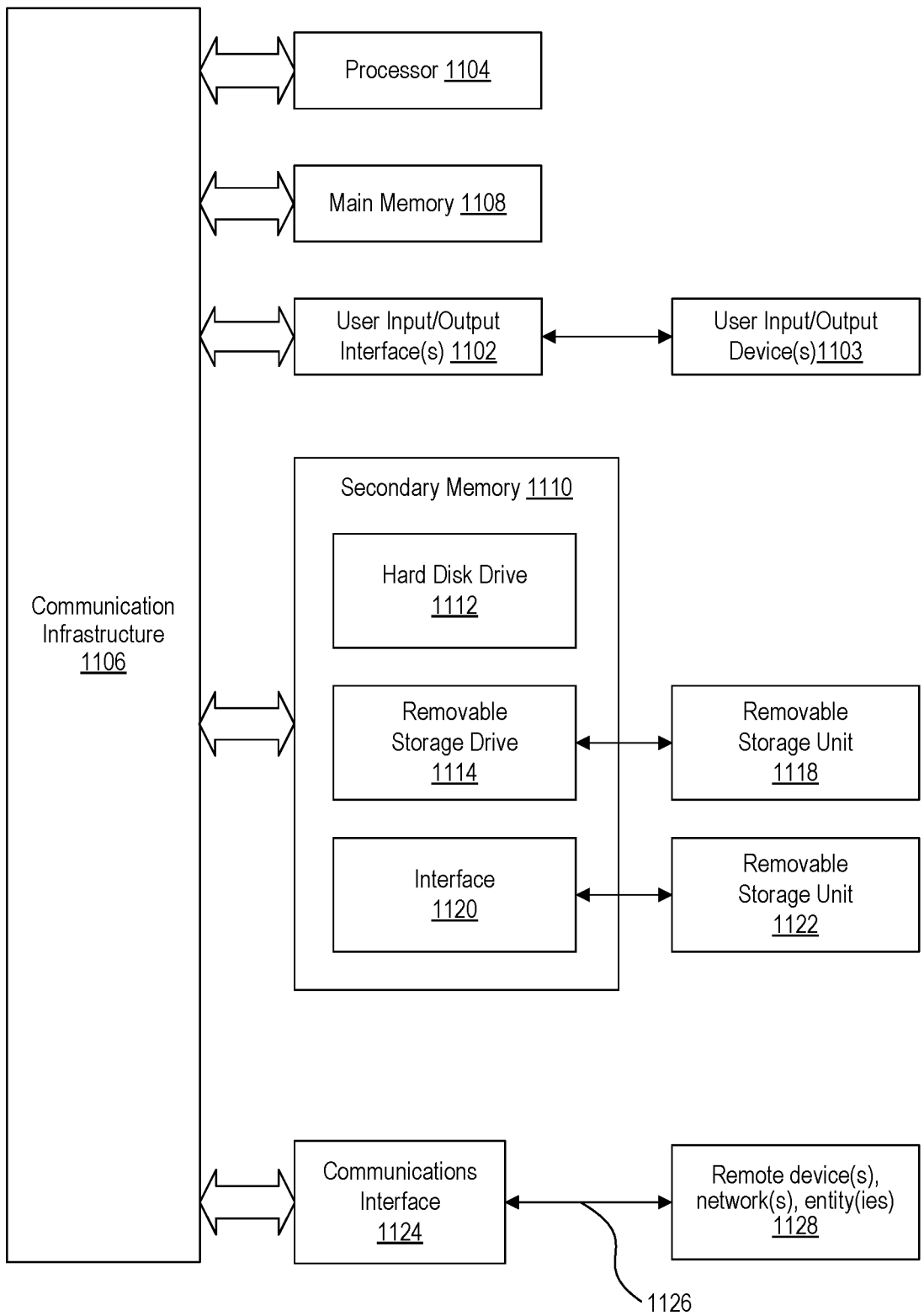
FIG. 11 shows a computer system for implementing various embodiments of this disclosure.

FIG. 11 shows a computer system 1100, according to some embodiments. Various embodiments and components therein can be implemented, for example, using computer system 1100 or any other well-known computer systems. For example, the method steps of FIG. 2 may be implemented via computer system 1100.

In some embodiments, computer system 1100 may comprise one or more processors (also called central processing units, or CPUs), such as a processor 1104. Processor 1104 may be connected to a communication infrastructure or bus 1106.

In some embodiments, one or more processors 1104 may each be a graphics processing unit (GPU). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

In some embodiments, computer system 1100 may further comprise user input/output device(s) 1103, such as monitors, keyboards, pointing devices, etc., that communicate with communication infrastructure 1106 through user input/output interface(s) 1102. Computer system 1100 may further comprise a main or primary memory 1108, such as random access memory (RAM). Main memory 1108 may comprise one or more levels of cache. Main memory 1108 has stored therein control logic (e.g., computer software) and/or data.

In some embodiments, computer system 1100 may further comprise one or more secondary storage devices or memory 1110. Secondary memory 1110 may comprise, for example, a hard disk drive 1112 and/or a removable storage device or drive 1114. Removable storage drive 1114 may be a floppy disk drive, a magnetic tape drive, a compact disk drive, an optical storage device, tape backup device, and/or any other storage device/drive. Removable storage drive 1114 may interact with a removable storage unit 1118. Removable storage unit 1118 may comprise a computer usable or readable storage device having stored thereon computer software (control logic) and/or data. Removable storage unit 1118 may be a floppy disk, magnetic tape, compact disk, DVD, optical storage disk, and/any other computer data storage device. Removable storage drive 1114 reads from and/or writes to removable storage unit 1118 in a well-known manner.

In some embodiments, secondary memory 1110 may comprise other means, instrumentalities or other approaches for allowing computer programs and/or other instructions and/or data to be accessed by computer system 1100. Such means, instrumentalities or other approaches may comprise, for example, a removable storage unit 1122 and an interface 1120. Examples of the removable storage unit 1122 and the interface 1120 may comprise a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

In some embodiments, computer system 1100 may further comprise a communication or network interface 1124. Communication interface 1124 enables computer system 1100 to communicate and interact with any combination of remote devices, remote networks, remote entities, etc. (individually and collectively referenced by reference number 1128). For example, communication interface 1124 may allow computer system 1100 to communicate with remote devices 1128 over communications path 1126, which may be wired and/or wireless, and which may comprise any combination of LANs, WANs, the Internet, etc. Control logic and/or data may be transmitted to and from computer system 1100 via communications path 1126.

In some embodiments, a non-transitory, tangible apparatus or article of manufacture comprising a non-transitory, tangible computer useable or readable medium having control logic (software) stored thereon is also referred to herein as a computer program product or program storage device. This includes, but is not limited to, computer system 1100, main memory 1108, secondary memory 1110, and removable storage units 1118 and 1122, as well as tangible articles of manufacture embodying any combination of the foregoing. Such control logic, when executed by one or more data processing devices (such as computer system 1100), causes such data processing devices to operate as described herein.

Based on the teachings contained in this disclosure, it will be apparent to those skilled in the relevant art(s) how to make and use embodiments of this disclosure using data processing devices, computer systems and/or computer architectures other than that shown in FIG. 11. In particular, embodiments may operate with software, hardware, and/or operating system implementations other than those described herein.

It is to be understood that the phraseology or terminology herein is for the purpose of description and not of limitation, such that the terminology or phraseology of the present disclosure is to be interpreted by those skilled in relevant art(s) in light of the teachings herein.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

While specific embodiments of the disclosure have been described above, it will be appreciated that embodiments of the present disclosure may be practiced otherwise than as described. The descriptions are intended to be illustrative, not limiting. Thus, it will be apparent to one skilled in the art that modifications may be made to the disclosure as described without departing from the scope of the claims set out below.

The foregoing description of the specific embodiments will so fully reveal the general nature of the present disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein.

The breadth and scope of the protected subject matter should not be limited by any of the above-described exemplary embodiments, but should be defined only in accordance with the following claims and their equivalents.

What is claimed is:

1. A method for efficiently distinguishing a disease state from a non-disease state in an image, comprising:
   receiving, over a network from a user device associated with a user, an image of a target area of the user;
   correcting, using one or more processors, for background noise in the image by applying a semantic segmentation filter to obtain a segmented image, wherein the sematic segmentation filter is trained to remove the background noise from the image;
   generating an augmented image from a set of images, wherein the generating comprises:
      extracting a disease pattern from a first image in the set of images, wherein the first image is associated with the disease state, and wherein the disease state is underrepresented in the set of images;
      identifying a second image in the set of images, wherein the second image is associated with a healthy target area that satisfies at least a criterion, and wherein the criterion is identified based on the first image; and
      blending the disease pattern with the second image to obtain the augmented image;
   determining, using a trained artificial intelligence (AI) model and the segmented image, at least one classification for the target area, wherein the trained AI model is trained using the augmented image; and
   causing the display of the at least one classification and disease information on the user device associated with the user, wherein the trained AI model is further trained using a feedback comprising the at least one classification.

2. The method of claim 1, further comprising:
   collecting the set of images;
   selecting a subset of images from the set of images based on an imbalance in the set of images;

performing image augmentation for each image of the subset of images to obtain an augmented set of images;

applying one or more transformations to one or more images of the set of images and the augmented set of images to create a modified set of images, wherein the one or more transformations include resealing, rotating, vertical flipping, horizontal flipping, vertical shifting, horizontal shifting, slanting a shape of an image, changing a brightness level of the image, and changing a zoom level of the image;

creating a training set comprising the set of images, the modified set of images, and the augmented set of images; and training the AI model using the training set.

3. The method of claim 1, wherein applying the semantic segmentation filter further comprises removing pixels from the image that are not associated with the target area.

4. The method of claim 1, further comprising:
generating, using the trained AI model, a saliency map associated with the image, wherein the saliency map includes the image with highlighted pixels that correspond to an area indicative of the at least one classification;
obtaining a cropped image from the image based on a bounding box of the highlighted pixels and the segmented image; and
determining, using the trained AI model and the cropped image, another classification and another saliency map.

5. The method of claim 1, further comprising:
transmitting the image to a medical professional over a secured network;
receiving disease data associated with the image from the medical professional; and
automatically adding the image and the disease data to a training dataset for the trained AI model.

6. The method of claim 5, further comprising:
retraining the trained AI model using the training dataset in response to determining that a number of newly added images exceed a threshold.

7. The method of claim 1, wherein the at least one classification corresponds to a sexually transmitted disease.

8. A system for efficiently distinguishing a disease state from a non-disease state in an image, comprising:
a memory; and
at least one processor coupled to the memory and configured to:
receive, over a network from a user device associated with a user, an image of a target area of the user;
correct for background noise in the image by applying a semantic segmentation filter to obtain a segmented image, wherein the sematic segmentation filter is trained to remove the background noise from the image;
generate an augmented image from a set of images, wherein to generate the augmented image, the at least one processor is further configured to:
extract a disease pattern from a first image in the set of images, wherein the first image is associated with the disease state, and wherein the disease state is underrepresented in the set of images;
identify a second image in the set of images, wherein the second image is associated with a healthy target area that satisfies at least a criterion, and wherein the criterion is identified based on the first image; and
blend the disease pattern with the second image to obtain the augmented image;

determine, using a trained artificial intelligence (AI) model and the segmented image, at least one classification for the target area, wherein the trained AI model is trained using the augmented image; and
cause the display of the at least one classification and disease information on the user device associated with the user, wherein the trained AI model is further trained using a feedback comprising the at least one classification.

9. The system of claim 8, wherein the at least one processor is further configured to:
collect the set of images;
select a subset of images from the set of images based on an imbalance in the set of images;
perform image augmentation for each image of the subset of images to obtain an augmented set of images;
apply one or more transformations to one or more images of the set of images and the augmented set of images to create a modified set of images, wherein the one or more transformations include resealing, rotating, vertical flipping, horizontal flipping, vertical shifting, horizontal shifting, slanting a shape of an image, changing a brightness level of the image, and changing a zoom level of the image;
create a training set comprising the set of images, the modified set of images, and the augmented set of images; and
train the AI model using the training set.

10. The system of claim 8, wherein to apply the semantic segmentation filter, the at least one processor is further configured to:
remove pixels from the image that are not associated with the target area.

11. The system of claim 8, wherein the at least one processor is further configured to:
generate, using the trained AI model, a saliency map associated with the image, wherein the saliency map includes the image with highlighted pixels that correspond to an area indicative of the at least one classification;
obtain a cropped image from the image based on a bounding box of the highlighted pixels and the segmented image; and
determine, using the trained AI model and the cropped image, another classification and another saliency map.

12. The system of claim 8, wherein the at least one processor is further configured to:
transmit the image to a medical professional over a secured network;
receive disease data associated with the image from the medical professional; and
automatically add the image and the disease data to a training dataset for the trained AI model.

13. The system of claim 8, wherein the at least one classification corresponds to a sexually transmitted disease.

14. A non-transitory computer-readable medium having instructions stored thereon that, when executed by at least one computing device, cause the at least one computing device to perform operations comprising:
receiving, over a network from a user device associated with a user, an image of a target area of the user;
correcting for background noise in the image by applying a semantic segmentation filter to obtain a segmented image, wherein the sematic segmentation filter is trained to remove the background noise from the image;

generating an augmented image from a set of images, wherein the generating comprises:
  extracting a disease pattern from a first image in the set of images, wherein the first image is associated with the disease state, and wherein the disease state is underrepresented in the set of images;
  identifying a second image in the set of images, wherein the second image is associated with a healthy target area that satisfies at least a criterion, and wherein the criterion is identified based on the first image; and
  blending the disease pattern with the second image to obtain the augmented image;
determining, using a trained artificial intelligence (AI) model and the segmented image, at least one classification for the target area, wherein the trained AI model is trained using the augmented image; and
causing the display of the at least one classification and disease information on the user device associated with the user, wherein the trained AI model is further trained using a feedback comprising the at least one classification.

15. The non-transitory computer-readable medium of claim 14, the operations further comprising:
collecting the set of images;
selecting a subset of images from the set of images based on an imbalance in the set of images;
performing image augmentation for each image of the subset of images to obtain an augmented set of images;
applying one or more transformations to one or more images of the set of images and the augmented set of images to create a modified set of images, wherein the one or more transformations include rescaling, rotating, vertical flipping, horizontal flipping, vertical shifting, horizontal shifting, slanting a shape of an image, changing a brightness level of the image, and changing a zoom level of the image;
creating a training set comprising the set of images, the modified set of images, and the augmented set of images; and
training the AI model using the training set.

16. The non-transitory computer-readable medium of claim 14, the operations further comprising:
generating, using the trained AI model, a saliency map associated with the image, wherein the saliency map includes the image with highlighted pixels that correspond to an area indicative of the at least one classification;
obtaining a cropped image from the image based on a bounding box of the highlighted pixels; and
determining, using the trained AI model and the cropped image, another classification and another saliency map.

17. The non-transitory computer-readable medium of claim 14, the operations further comprising:
transmitting the image to a medical professional over a secured network;
receiving disease data associated with the image from the medical professional; and
automatically adding the image and the disease data to a training dataset for the trained AI model.

18. The non-transitory computer-readable medium of claim 17, the operations further comprising:
retraining the trained AI model using the training dataset in response to determining that a number of newly added images exceed a threshold.

19. The non-transitory computer-readable medium of claim 14, wherein the at least one classification corresponds to a sexually transmitted disease.

20. The non-transitory computer-readable medium of claim 14, wherein applying the semantic segmentation filter further comprises removing pixels from the image that are not associated with the target area.

* * * * *

UNITED STATES PATENT AND TRADEMARK OFFICE
CERTIFICATE OF CORRECTION

PATENT NO. : 11,721,023 B1
APPLICATION NO. : 17/967696
DATED : August 8, 2023
INVENTOR(S) : Kularathne et al.

Page 1 of 1

It is certified that error appears in the above-identified patent and that said Letters Patent is hereby corrected as shown below:

In the Claims

At Column 19, Line 6, replace "resealing" with --rescaling--.

At Column 20, Line 20, replace "resealing" with --rescaling--.

Signed and Sealed this
Fourteenth Day of November, 2023

Katherine Kelly Vidal
*Director of the United States Patent and Trademark Office*